United States Patent [19]

Aoki et al.

[11] 3,950,360

[45] Apr. 13, 1976

[54] ANTIBIOTIC SUBSTANCES

[75] Inventors: Atsushi Aoki; Rikiya Fukuda; Toshio Nakayabu, all of Sapporo; Keijiro Ishibashi, Tokyo; Chiyoko Takeichi, Tokyo; Mitsuo Ishida, Tokyo, all of Japan

[73] Assignee: Sankyo Company Limited, Tokyo, Japan

[22] Filed: Sept. 4, 1973

[21] Appl. No.: 394,073

Related U.S. Application Data

[63] Continuation-in-part of Ser. No. 365,188, May 30, 1973, abandoned.

[30] Foreign Application Priority Data

June 8, 1972  Japan............................... 47-57058

[52] U.S. Cl........ 260/343.2 R; 195/81; 260/326.34; 424/279; 424/274

[51] Int. Cl.² ...................................... C07D 313/00
[58] Field of Search ........................... 260/343.2 R

[56] References Cited
UNITED STATES PATENTS 3,839,363   10/1974   Shah et al. ...................... 260/343.2

*Primary Examiner*—John M. Ford
*Attorney, Agent, or Firm*—Flynn & Frishauf

[57] ABSTRACT

New antibiotic substances are obtained by culturing a strain belonging to the genus Streptomyces and recovering said substances from the culture material. The new antibiotic substances possess insecticidal and acaricidal properties.

6 Claims, 27 Drawing Figures

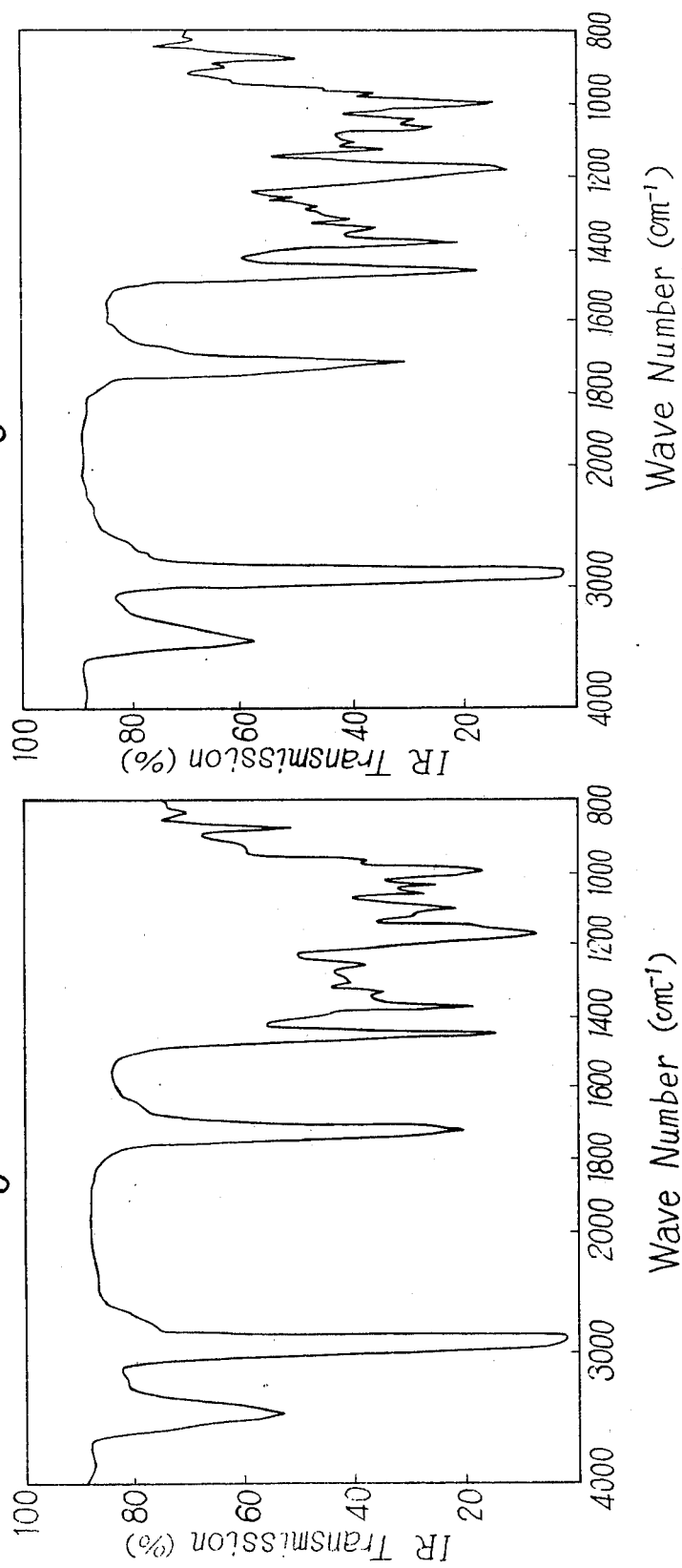

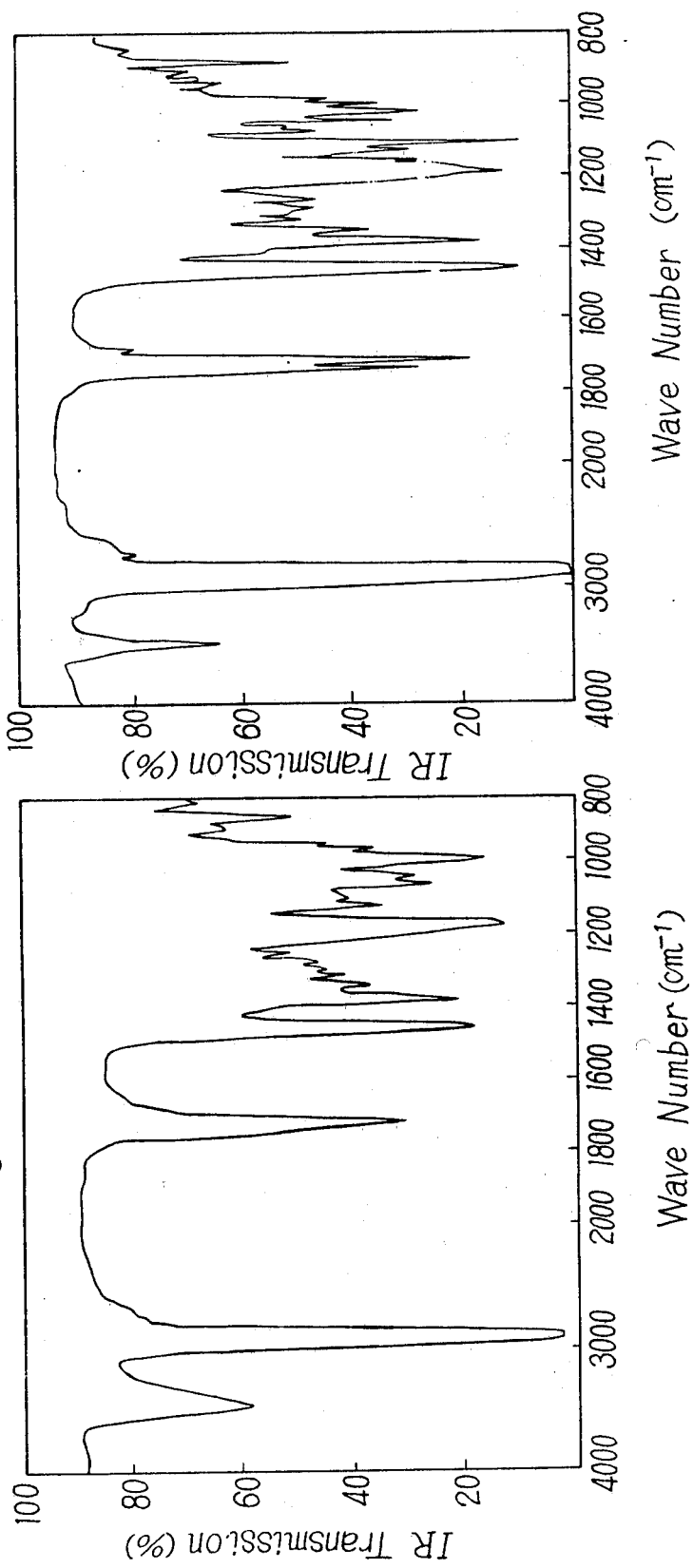

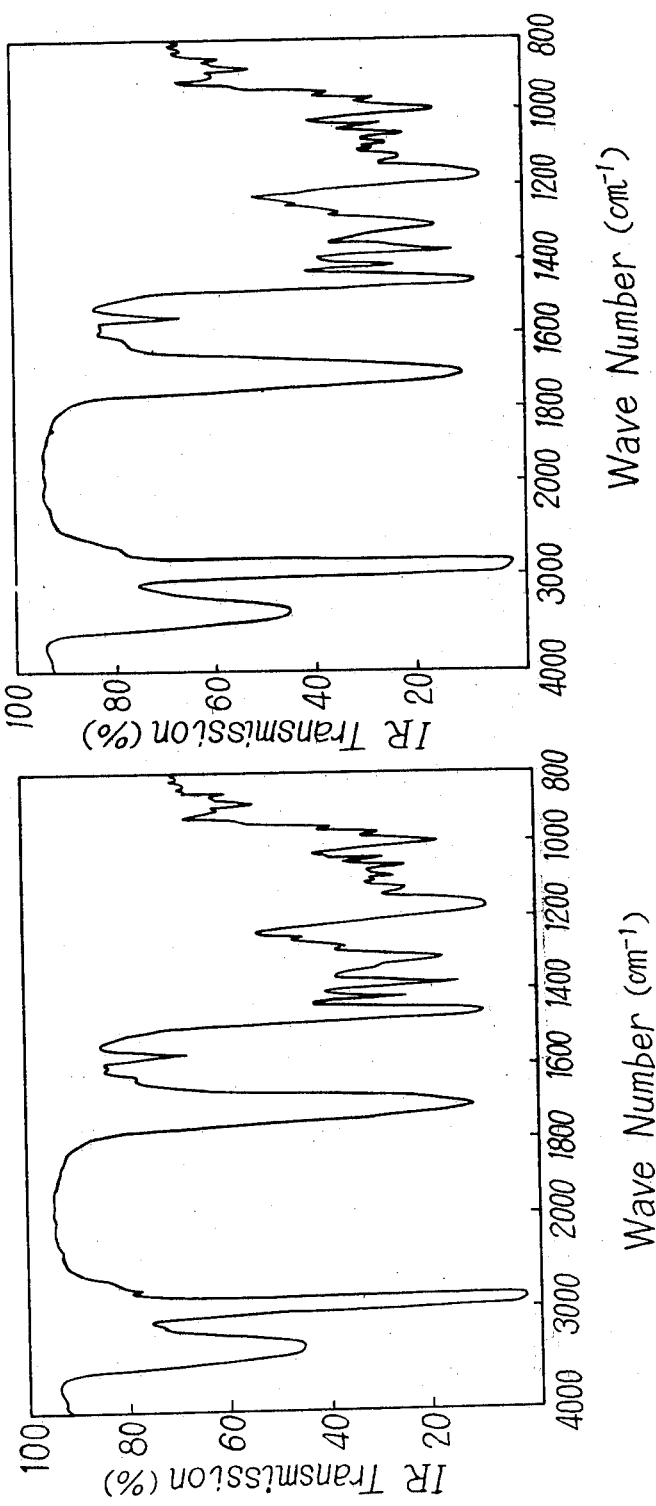

ANTIBIOTIC SUBSTANCES

This application is a continuation-in-part of U.S. patent application Ser. No. 365,188 filed May 30, 1973, now abandoned.

This invention relates to new antibiotic substances B-41, a process for producing the antibiotic substance B-41 by culturing in a medium a B-41-producing strain belonging to the genus *Streptomyces* and then recovering the resulting B-41 from the cultured substance, and an insecticidal and acaricidal composition containing novel antibiotic substances B-41 as an active ingredient.

Many organic compounds have heretofore been used as insecticidal and acaricidal preparations. Among antibiotic substances, however, only a few substances have been known to have insecticidal and acaricidal effects. Moreover, they have not been put into practical use yet.

As the result of extensive studies, we have found that a novel antibiotic substance B-41, which is produced by a B-41-146 strain, a new strain belonging to the genus *Streptomyces*, is not only far higher in acaricidal activity than the organic compounds having acaricidal activities but also is effective for the control of agricultural and horticultural harmful insects such as aphids, larvae of insects of the order Lepidoptera, etc.

The antibiotic substance B-41, which is the active ingredient of the insecticidal and acaricidal composition of the present invention could be separated into 9 kinds of substances; $A_1$, $A_2$, $A_3$, $A_4$, $B_1$, $B_2$, $B_3$, $C_1$ and $C_2$.

Figure 2:
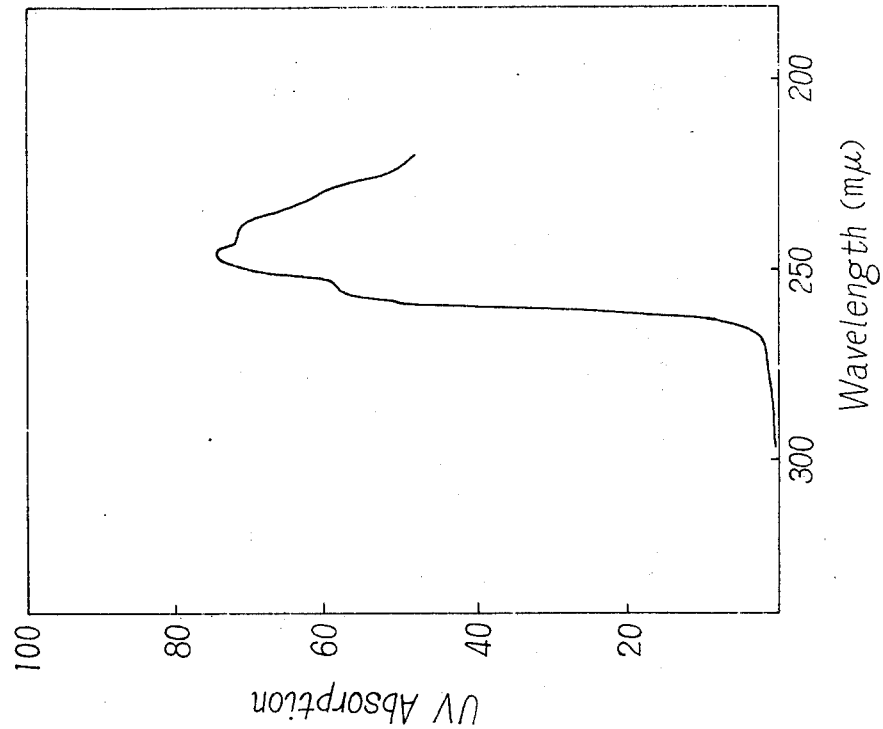
Figure 1:
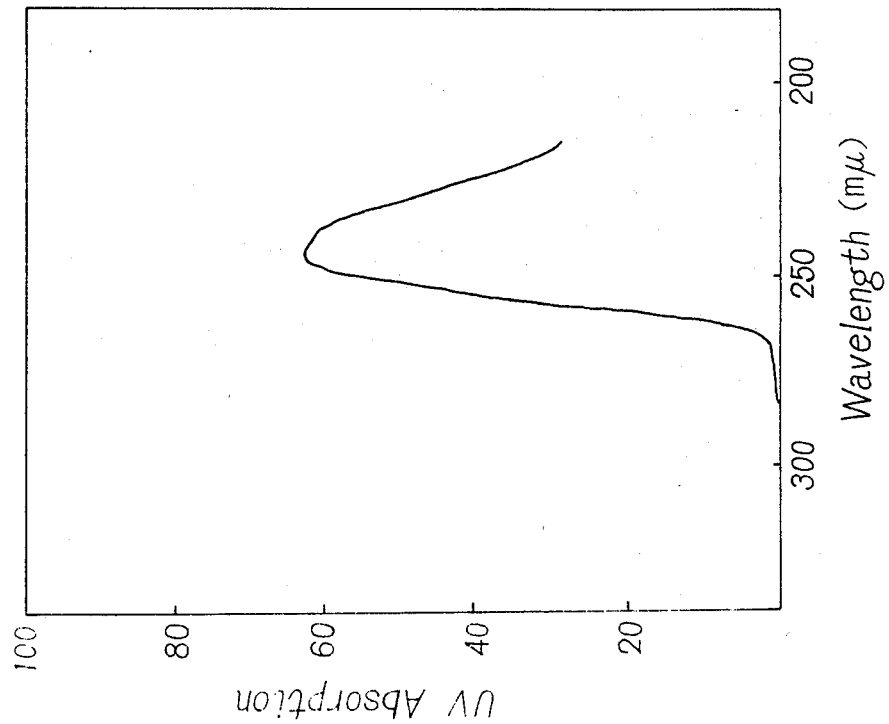
Figure 4:
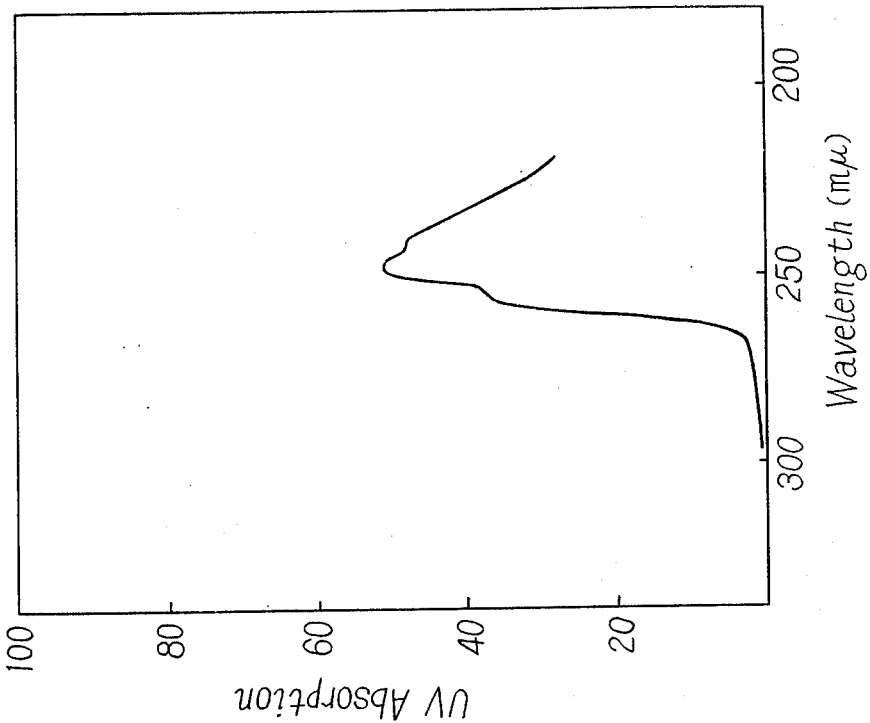
Figure 3:
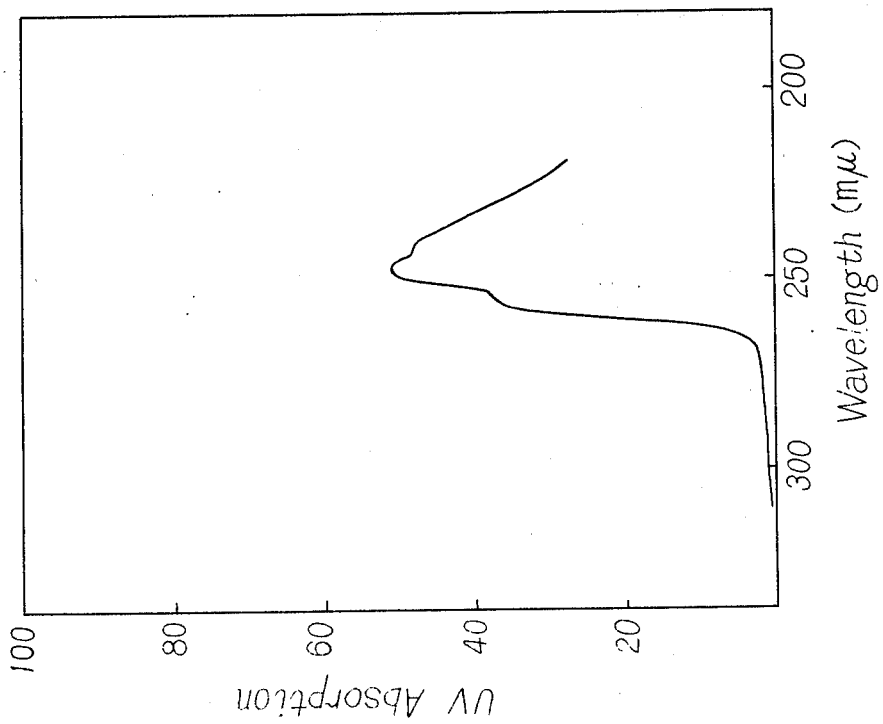
Figure 10:
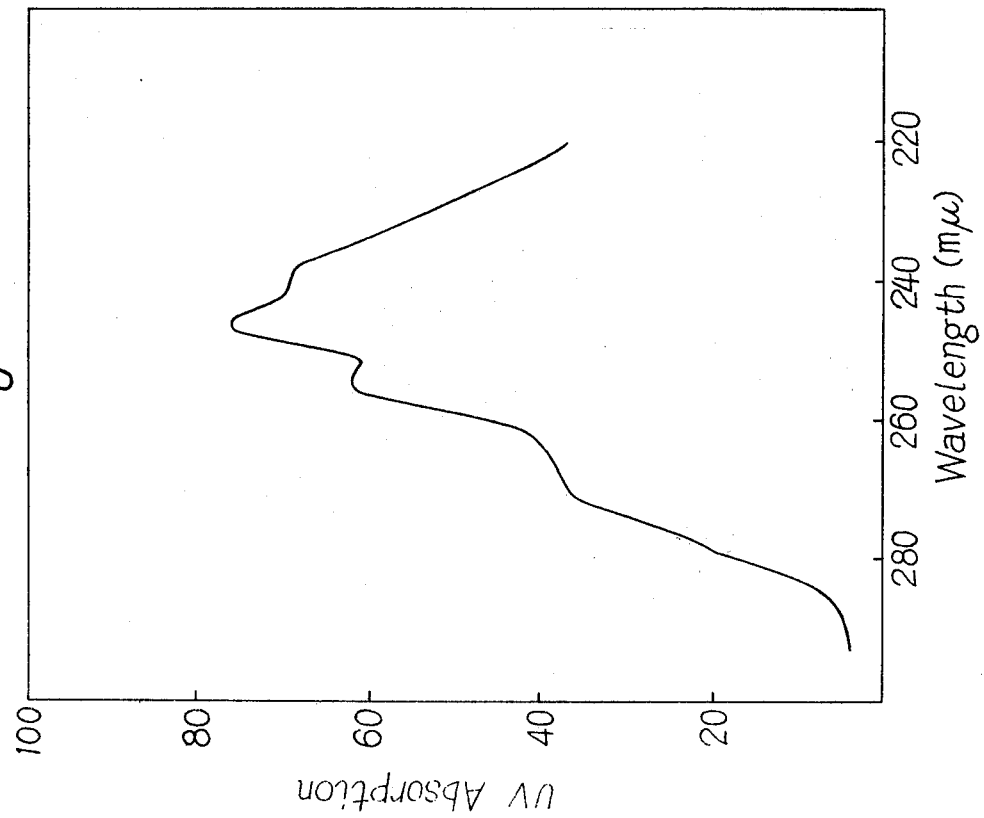
Figure 19:
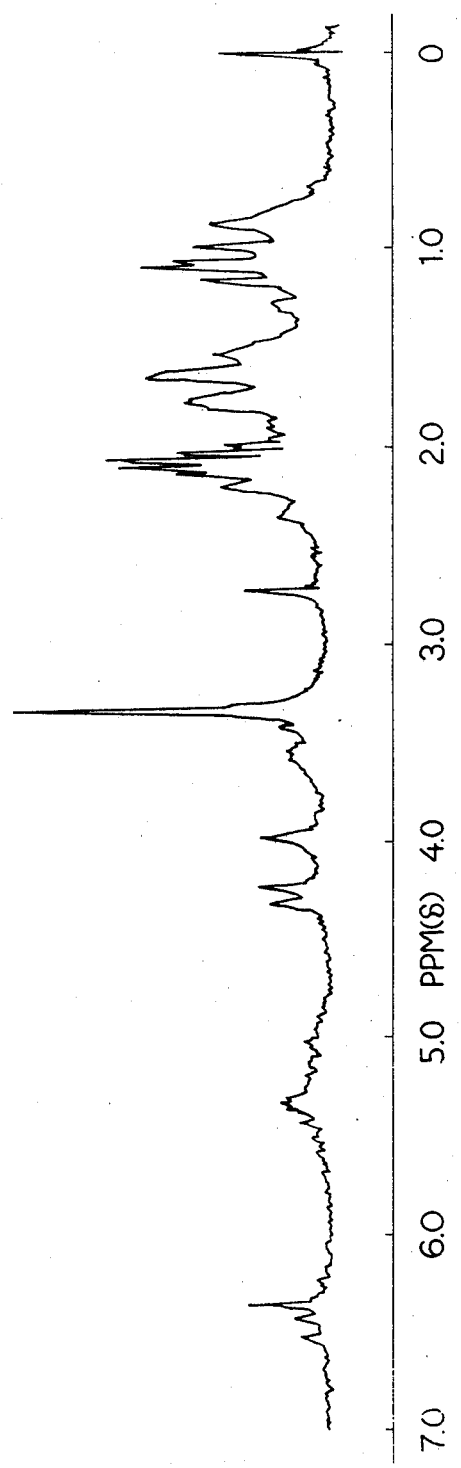
Figure 20:
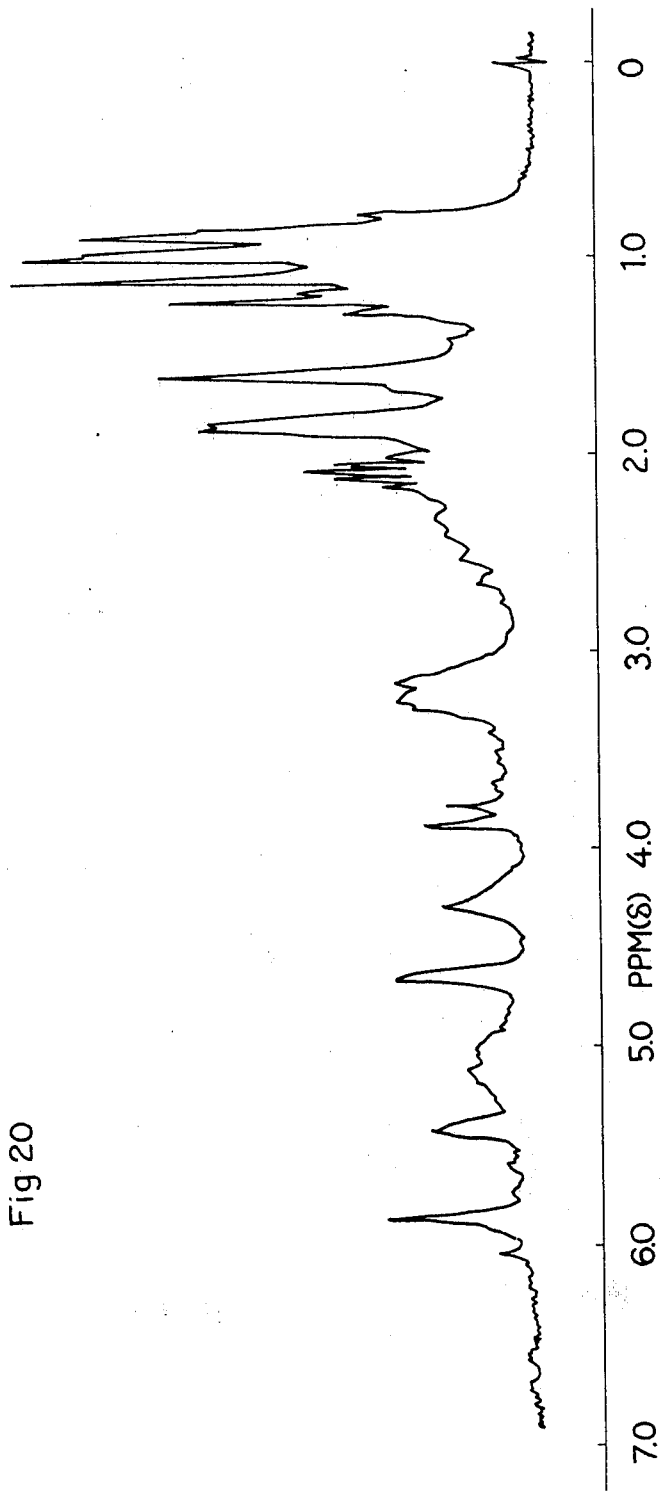
Figure 21:
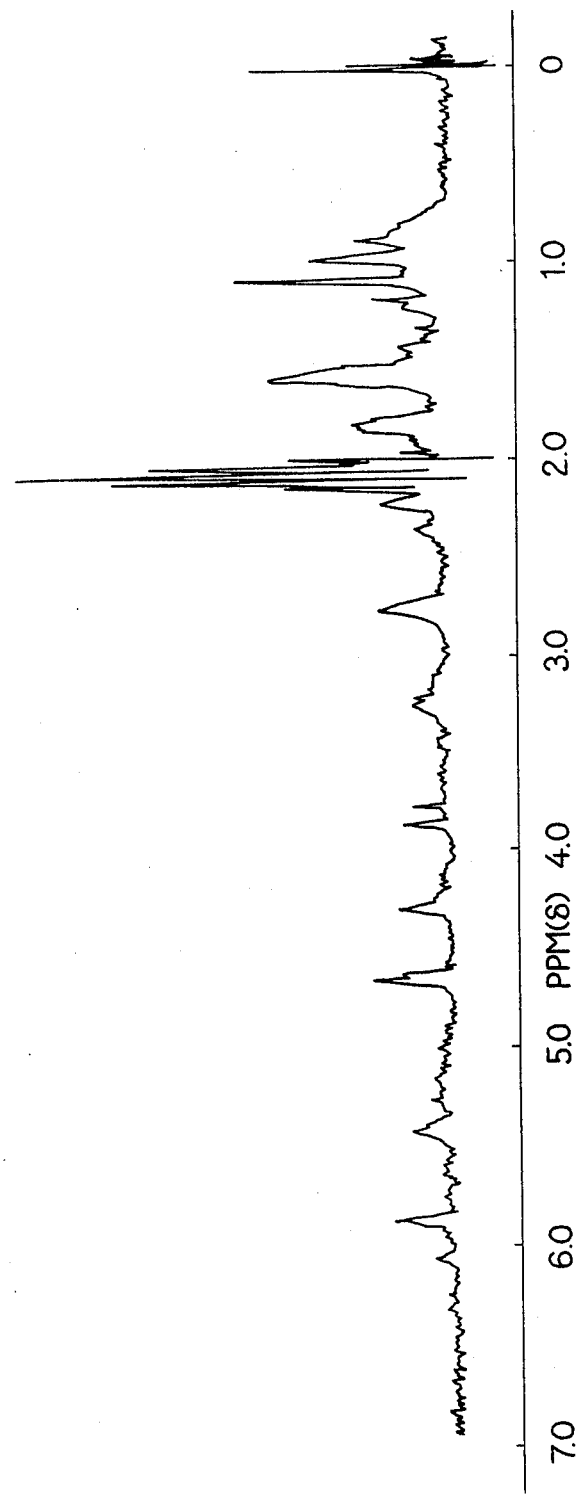
Figure 22:
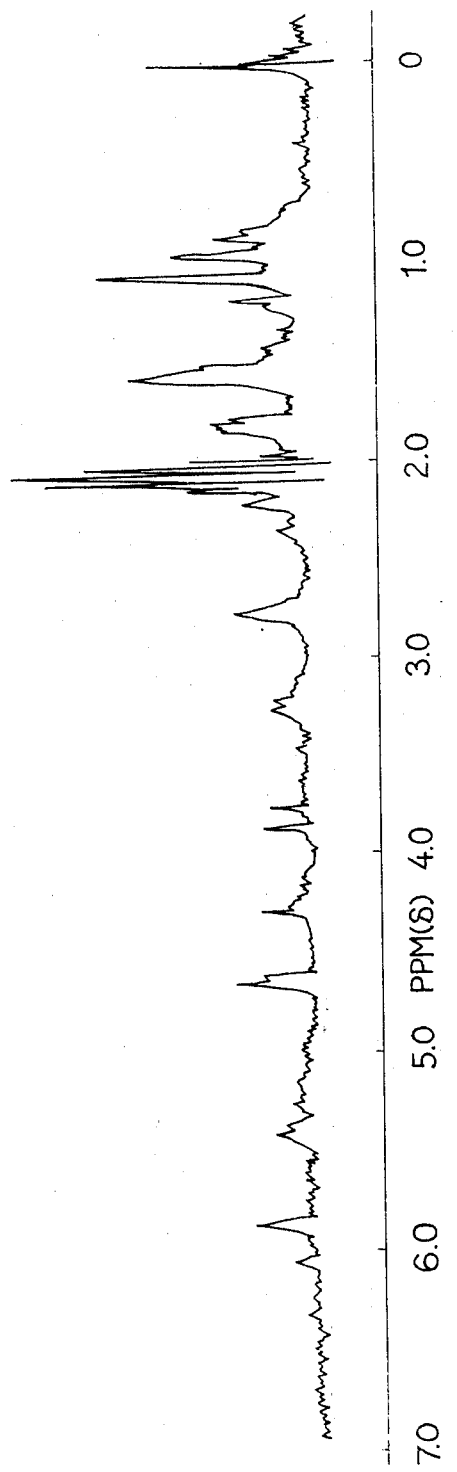
Figure 24:
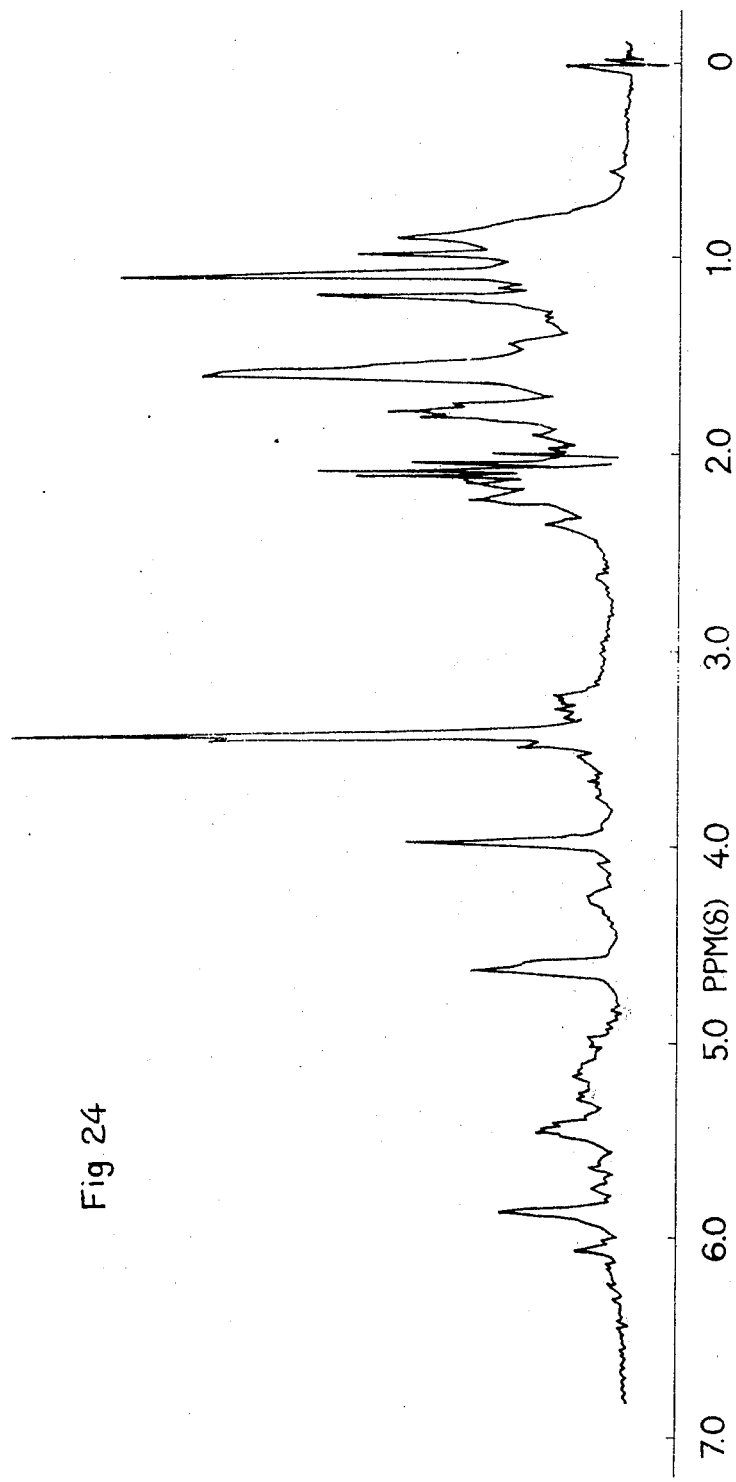
Figure 25:
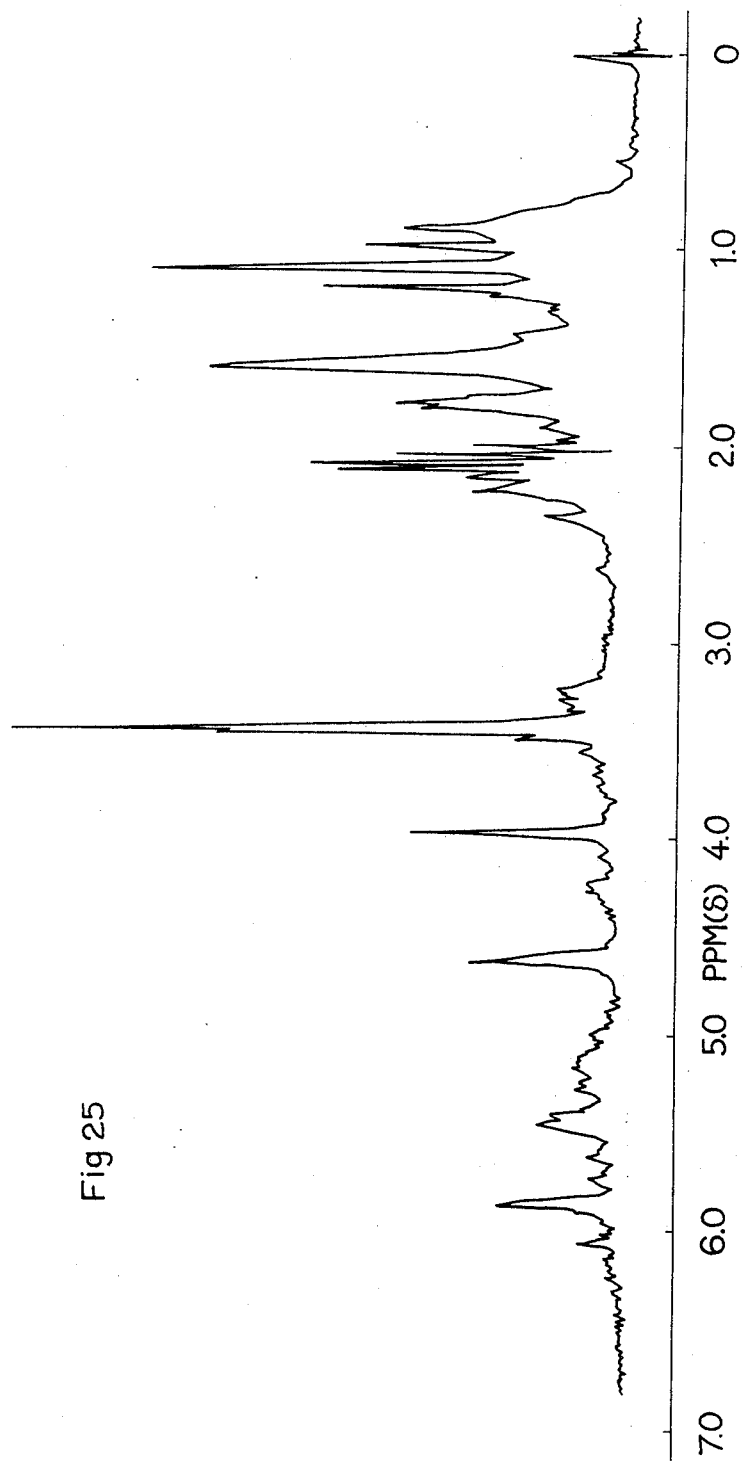
Figure 26:
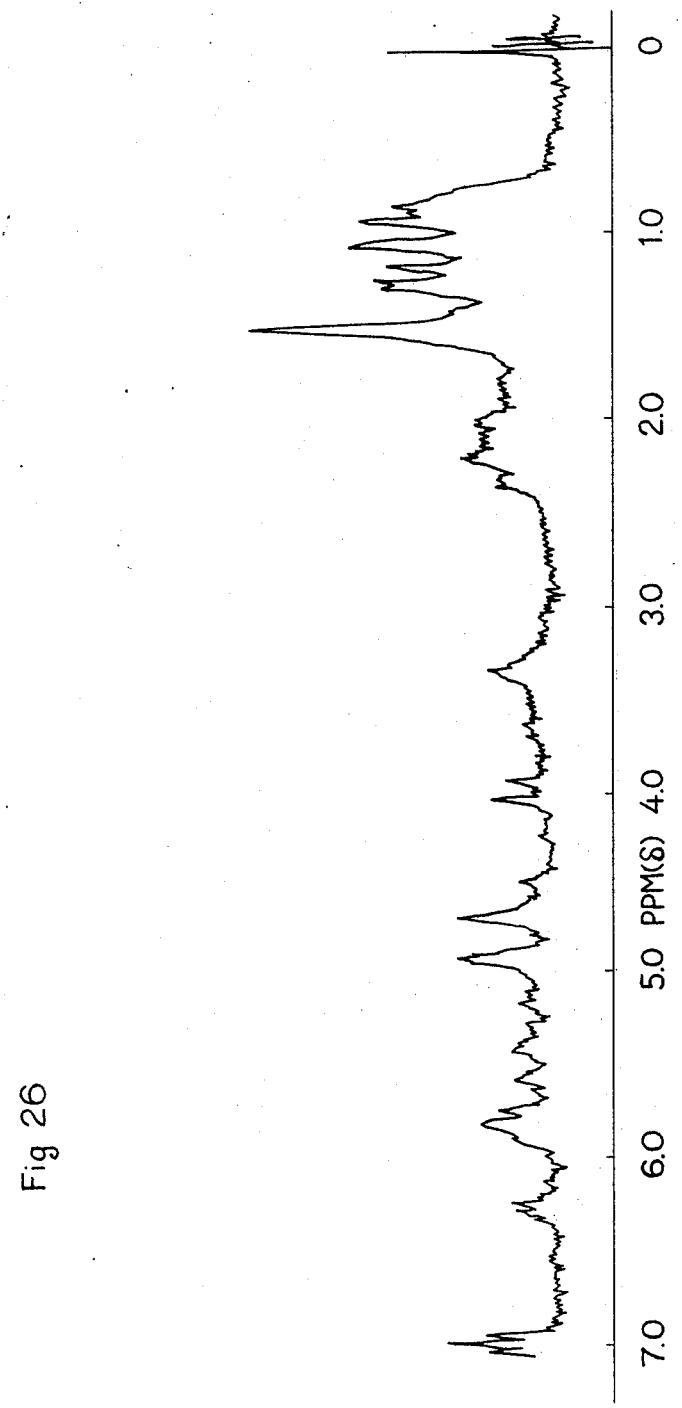
Figure 27:
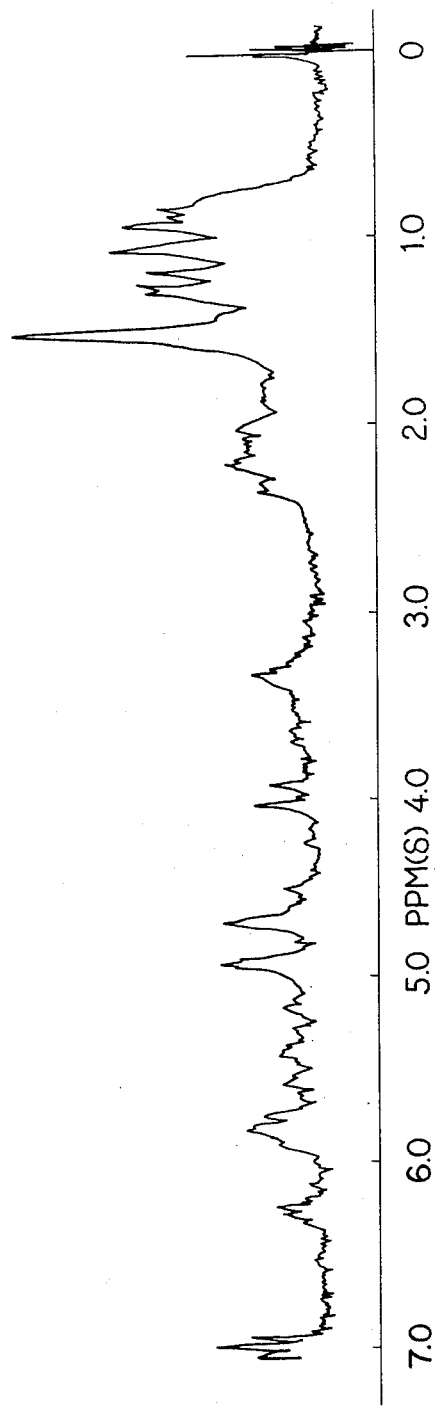

Physicochemical properties of these substances are as shown in the following table:

| Molecular formula | | | $A_1$ $C_{32}H_{48}O_7$ | $A_2$ $C_{38}H_{56}O_{10}$ | $A_3$ $C_{31}H_{44}O_7$ | $A_4$ $C_{32}H_{48}O_7$ |
|---|---|---|---|---|---|---|
| Elementary analysis (%) | Calculated | C | 70.56 | 67.33 | 70.43 | 70.82 |
|  |  | H | 8.88 | 8.39 | 8.39 | 8.54 |
|  | Found | C | 70.74 | 71.73 | 65.73 | 69.85 |
|  |  | H | 9.18 | 8.26 | 7.89 | 8.37 |
| Molecular weight | Osmometric method (in acetone) | | 513.9 | 672.1 | 517.0 | — |
|  | Mass spectrum (M+) | | 544 | 672 | 528 | 542 |
| Melting point (°C.) | | | Amorphous powder | Amorphous powder | 212–215 | 193–195 |
| Specific rotatory power $[\alpha]_D^{20}$ (Concentration of sample 5 mg/2 ml, length of layer in acetone 10 cm) | | | +160° | +54° | +106° | +103° |
| Ultraviolet absorption spectrum (λ-max, mμ) | | | 240.5 Fig. 1 | 245 Fig. 2 | 245 Fig. 3 | 245 Fig. 4 |
| Infrared absorption spectrum (Nujol method) | | | Fig. 10 | Fig. 11 | Fig. 12 | Fig. 13 |
| Nuclear magnetic resonance spectrum [in $(CD_3)_2CO$ in the case of Figs. 19 to 25, and in $CDCl_3$ in the case of Figs. 26 and 27; 60 MHz] | | | Fig. 19 | Fig. 20 | Fig. 21 | Fig. 22 |
| Mass spectrum (Main peaks under the conditions of 75 eV, ionization room temperature 200°C. and sample temperature 120° to 190°C.) | | | 544 402 181 153 | 672 181 153 151 | 528 400 181 153 151 | 542 414 195 167 151 |
| Solubility in solvents | | | Difficultly soluble in water; easily soluble in n-hexane, benzene, acetone, ethanol and chloroform | do. | do. | do. |
| Color reaction (according to thin layer chromatography) | Iodine/chloroform | | Yellow | Yellow | Yellow | Yellow |
|  | Ninhydrin | | Negative | Negative | Negative | Negative |
|  | Sulfuric acid spraying with heating | | Brown | Reddish purple | Brown | Brown |
|  | Potassium permanganate solution | | Yellow | Yellow | Yellow | Yellow |
| Alcohol solution, neutralization titration method | | | No pKa at pH ranging from 2 to 12 | do. | do. | do. |
| Color of substance | | | Colorless | Colorless | Colorless | Colorless |

$B_1$ $B_2$ $B_3$ $C_1$ $C_2$

-continued

Figure 6:
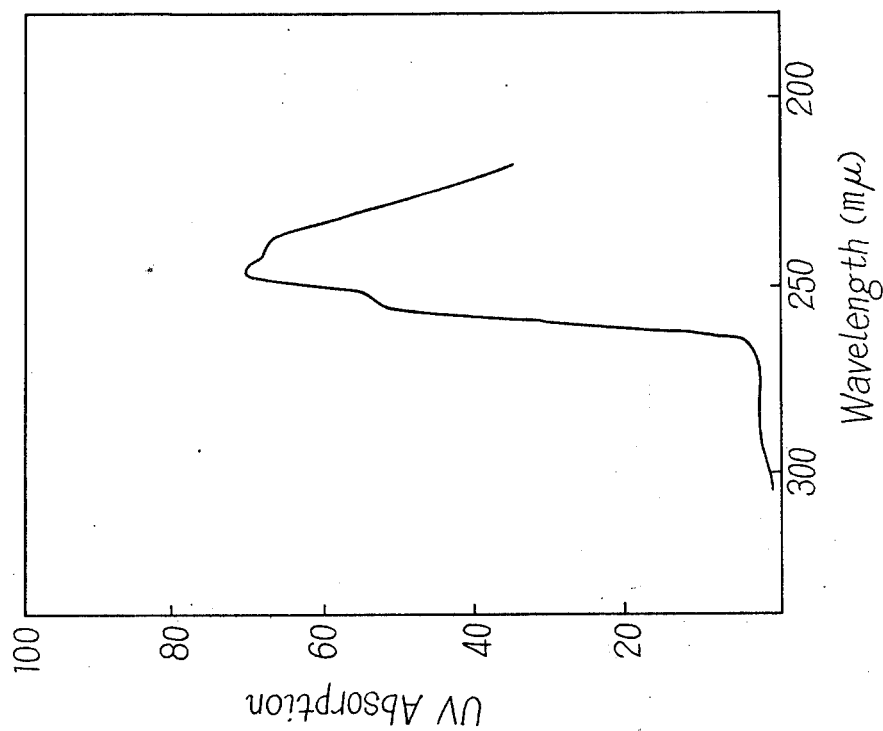
Figure 5:
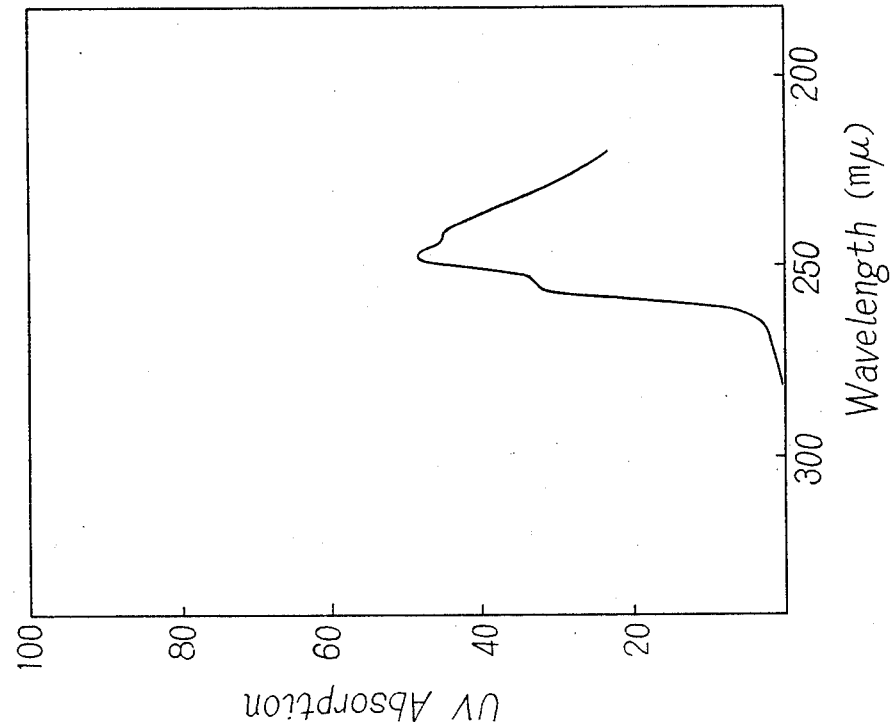
Figure 8:
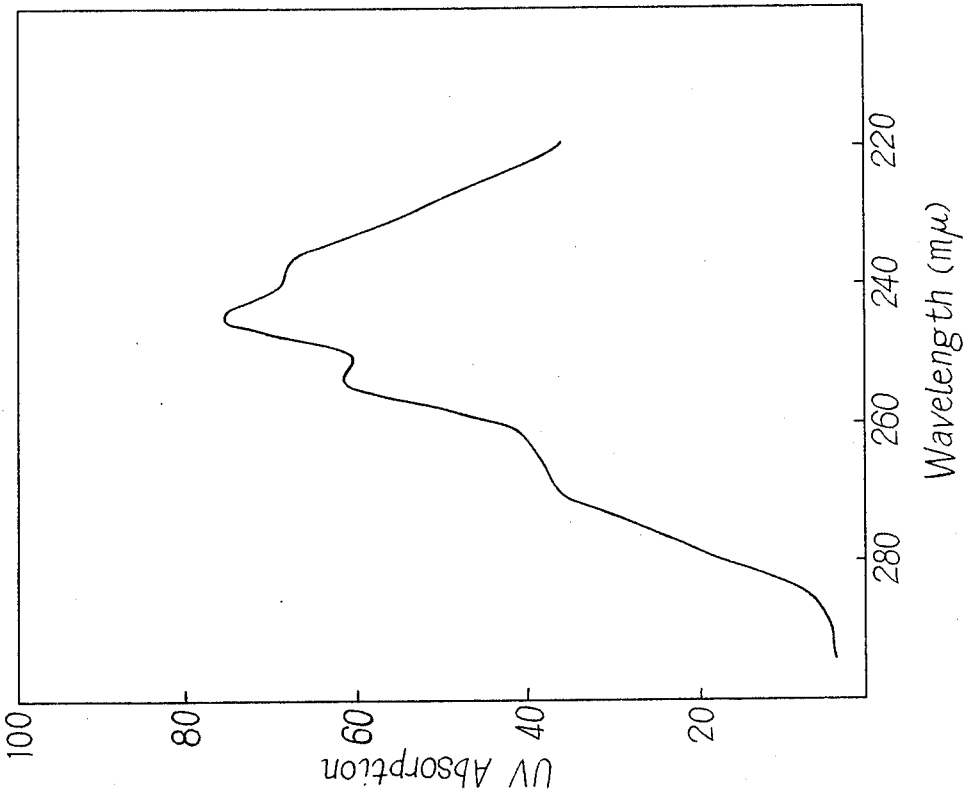
Figure 7:
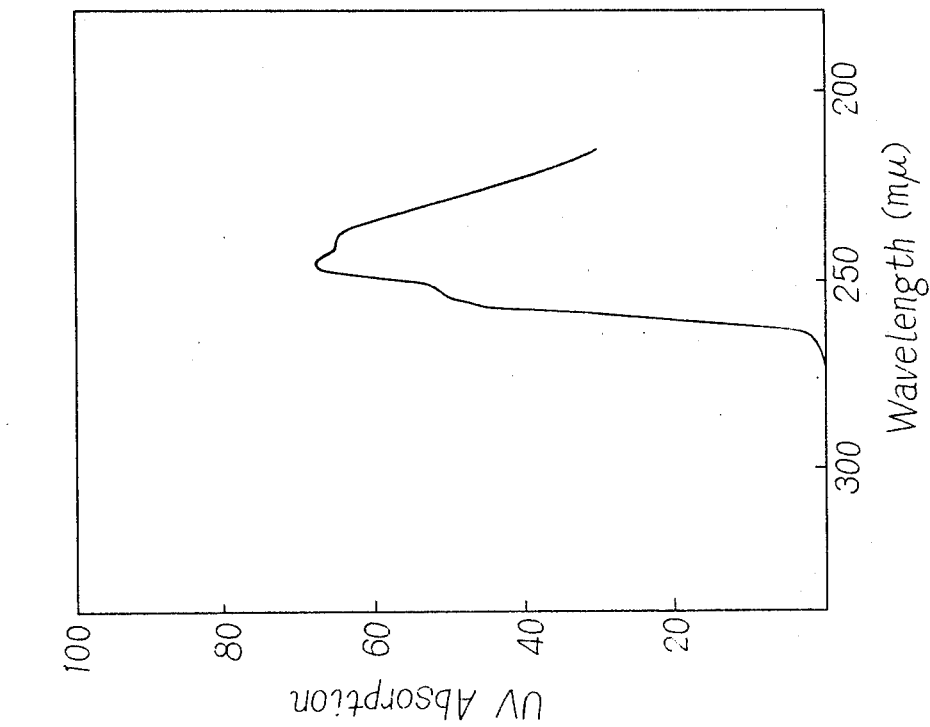
Figure 9:
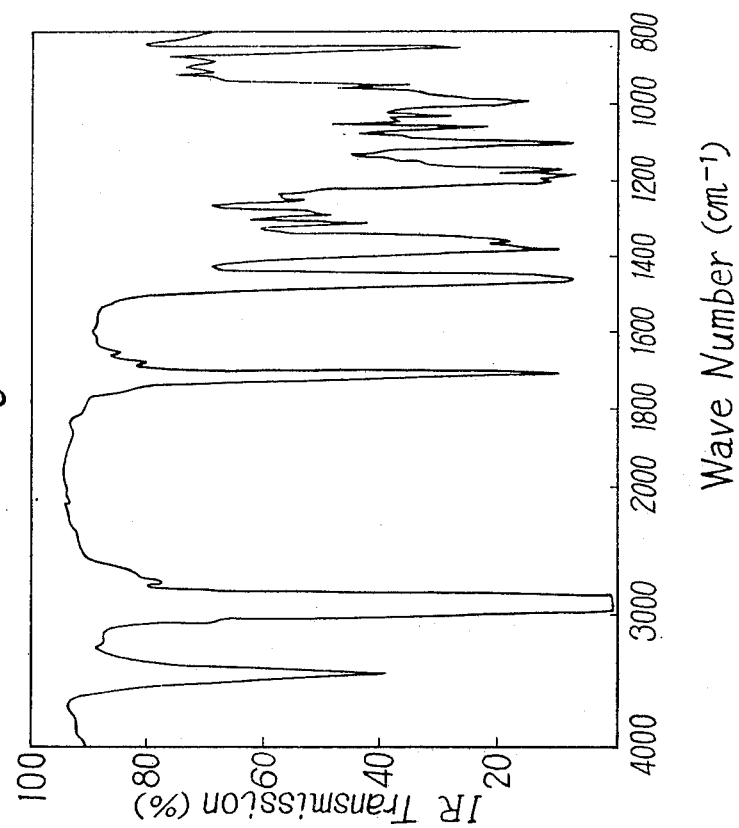
Figure 16:
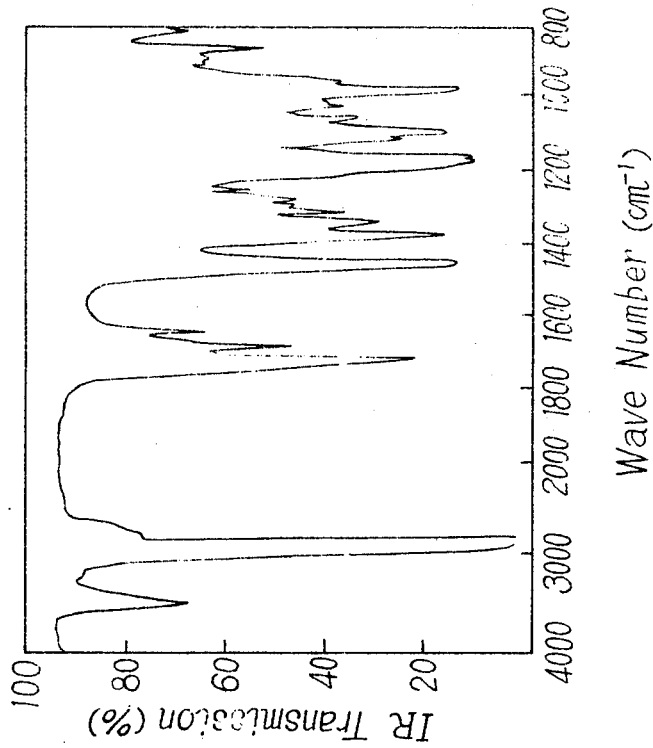
Figure 15:
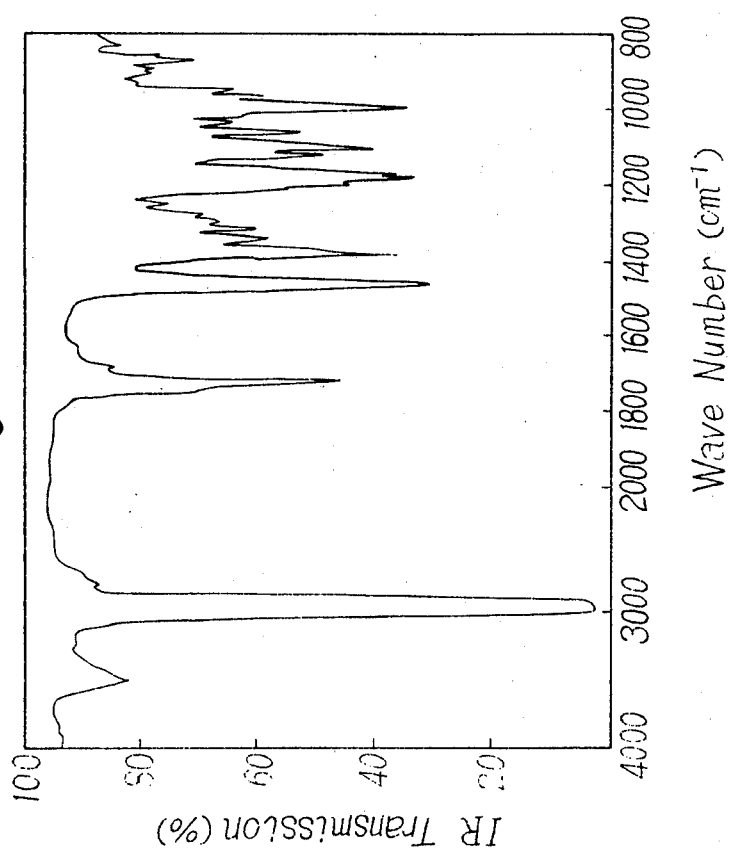
Figure 23:
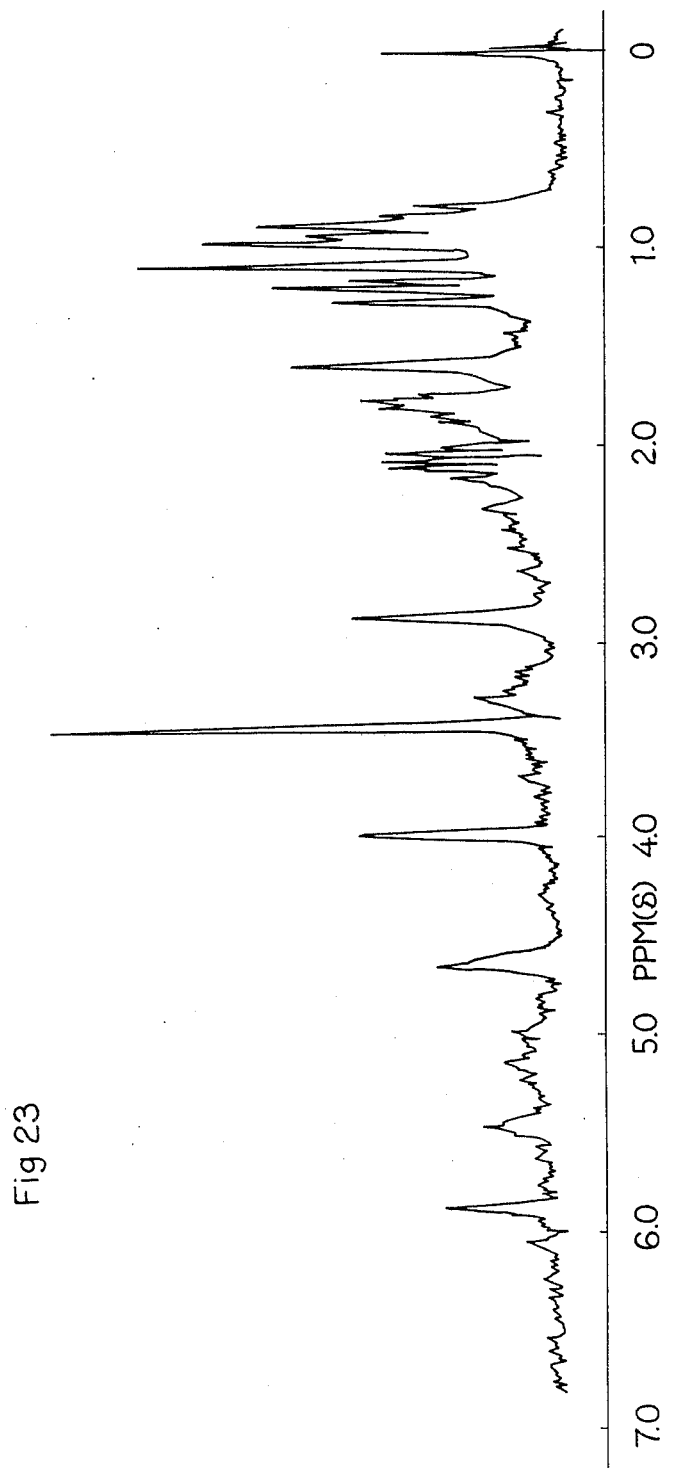

| | | A₁<br>$C_{32}H_{48}O_7$ | A₂<br>$C_{38}H_{56}O_{10}$ | A₃<br>$C_{31}H_{44}O_7$ | A₄<br>$C_{32}H_{46}O_7$ | |
|---|---|---|---|---|---|---|
| Molecular formula | | | | | | |
| Molecular formula | | $C_{39}H_{58}O_{10}$ | $C_{32}H_{46}O_7$ | $C_{33}H_{48}O_7$ | $C_{36}H_{47}O_9N$ | $C_{37}H_{49}O_9N$ |
| Elementary analysis (%) | Calculated C | 68.19 | 70.82 | 71.19 | C: 67.80<br>H: 7.43<br>N: 2.20 | C: 68.18<br>H: 7.58<br>N: 2.15 |
| | H | 8.51 | 8.54 | 8.69 | | |
| | Found C | 68.00 | 69.66 | 70.72 | C: 65.93<br>H: 7.53<br>N: 2.14 | C: 68.09<br>H: 7.54<br>N: 2.13 |
| | H | 8.32 | 8.32 | 8.59 | | |
| Molecular weight | Osmometric method (in acetone) | 629.5 | 524.3 | — | — | — |
| | Mass spectrum (M+) | 686 | 542 | 556 | 679 (Note 1) | 693 (Note 1) |
| Melting point (°C.) | | 176–178 | 139–142 | Amorphous powder | Amorphous powder | Amorphous powder |
| Specific rotatory power $[\alpha]_D^{20}$ (Concentration of sample 5 mg/2 ml, length of layer in acetone 10 cm) | | +75° | +131° | +126° | +57° | +54° |
| Ultraviolet absorption spectrum (λ-max, mμ) | | 245<br>Fig. 5 | 245<br>Fig. 6 | 245<br>Fig. 7 | 240<br>Fig. 8 | 240<br>Fig. 9 |
| Infrared absorption spectrum (Nujol method) | | Fig. 14 | Fig. 15 | Fig. 16 | Fig. 17 | Fig. 18 |
| Nuclear magnetic resonance spectrum [in $(CD_3)_2CO$ in the case of Figs. 19 to 25, and in $CDCl_3$ in the case of Figs. 26 and 27; 60 MHz] | | Fig. 23 | Fig. 24 | Fig. 25 | Fig. 26 | Fig. 27 |
| Mass spectrum (Main peaks under the conditions of 75 eV, ionization room temperature 200°C. and sample temperature 120° to 190°C.) | | 686<br>414<br>195<br>167<br>151<br>125 | 542<br>400<br>181<br>153<br>151 | 556<br>414<br>195<br>167<br>151 | 679<br>568<br>400<br>181<br>153<br>111<br>(Note 1) | 692<br>582<br>414<br>195<br>167<br>111<br>(Note 1) |
| Solubility in solvents | | do. | do. | do. | do. | |
| Color reaction (according to thin layer chromatography) | Iodine/chloroform | Yellow | Yellow | Yellow | Yellow | Yellow |
| | Ninhydrin | Negative | Negative | Negative | Negative | Negative |
| | Sulfuric acid spraying with heating | Reddish purple | Brown | Brown | Brown | Brown |
| | Potassium permanganate solution | Yellow | Yellow | Yellow | Yellow | Yellow |
| Alcohol solution, neutralization titration method | | do. | No pKa at pH ranging from 2 to 9 (crystallization took place at about pH 8.7 to make the measurement impossible | do. | No pKa at pH ranging from 2 to 12 | do. |
| Color of substance | | Colorless | Colorless | Colorless | Colorless | Colorless |

Note 1:
Each mass spectra of $C_1$ and $C_2$ were measured with the acetylated derivative obtained by substitution of $CH_3CO$-group for the hydrogen atom of $R_1$ in the plane structural formula as shown below.

The accompanying drawings show ultraviolet absorption, infrared absorption and nuclear magnetic resonance spectra of the antibiotic substance B-41, in which FIGS. 1 to 9 show, respectively the ultraviolet absorption spectra of $A_1$, $A_2$, $A_3$, $A_4$, $B_1$, $B_2$, $B_3$, $C_1$ and $C_2$ of the antibiotic substance B-41; FIGS. 10 to 18 show, respectively, the infrared absorption spectra of $A_1$, $A_2$, $A_3$, $A_4$, $B_1$, $B_2$, $B_3$, $C_1$ and $C_2$ of the antibiotic substance B-41; and FIGS. 19 to 27 show, respectively, the nuclear magnetic resonance spectra of $A_1$, $A_2$, $A_3$, $A_4$, $B_2$, $B_3$, $C_1$ and $C_2$ of the antibiotic substance B-41.

Further, Rf values of the above-mentioned substances as measured according to thin layer chromatography using a thin layer chromatographic spot film containing a fluorescence reagent (available from Tokyo Kasei Kogyo Co. Ltd: Trade name, "SPOTFILM fluorescent") were as set forth in table shown below. The detection was made according to the intensity of fluorescence omitted when each substance was irradiated with ultraviolet rays of 2536 A.

| Solvent system | \multicolumn{9}{c}{Silica gel F} |
|---|---|---|---|---|---|---|---|---|---|

| Solvent system | $A_1$ | $A_2$ | $A_3$ | $A_4$ | $B_1$ | $B_2$ | $B_3$ | $C_1$ | $C_2$ |
|---|---|---|---|---|---|---|---|---|---|
| Acetone/n-Hexane (30:70) | 0.47 | 0.32 | 0.42 | 0.44 | 0.47 | 0.61 | 0.63 | 0.22 | 0.24 |
| Ethyl acetate/Benzene (50:50) | 0.61 | 0.62 | 0.63 | 0.65 | 0.79 | 0.80 | 0.82 | 0.45 | 0.47 |
| Ethyl acetate/Chloroform (25:75) | 0.27 | 0.35 | 0.39 | 0.41 | 0.75 | 0.79 | 0.81 | 0.12 | 0.13 |
| Acetone/Benzene (40:60) | 0.85 | 0.75 | 0.77 | 0.79 | 0.92 | 0.92 | 0.92 | 0.60 | 0.63 |
| Acetone/Benzene (15:75) | 0.39 | 0.32 | 0.39 | 0.39 | 0.57 | 0.51 | 0.53 | 0.11 | 0.13 |
| Ethanol/n-Hexane (2:98) | 0 | 0 | 0 | 0 | 0 | 0 | 0 | 0 | 0 |

Alumina F

| Solvent system | $A_1$ | $A_2$ | $A_3$ | $A_4$ | $B_1$ | $B_2$ | $B_3$ | $C_1$ | $C_2$ |
|---|---|---|---|---|---|---|---|---|---|
| Acetone/n-Hexane (30:70) | 0.55 | 0.16 | 0.32 | 0.34 | 0.67 | 0.92 | 0.92 | 0 | 0 |
| Ethyl acetate/Benzene (50:50) | 0.56 | 0.10 | 0.21 | 0.23 | 0.73 | 0.81 | 0.83 | 0 | 0 |
| Ethyl acetate/Chloroform (25:75) | 0.40 | 0.10 | 0.15 | 0.17 | 0.63 | 0.65 | 0.67 | 0 | 0 |
| Acetone/Benzene (15:75) | 0.27 | 0.05 | 0.09 | 0.11 | 0.35 | 0.45 | 0.47 | 0 | 0 |
| Ethanol/n Hexane (2:98) | 0.17 | 0.03 | 0.07 | 0.09 | 0.20 | 0.42 | 0.44 | 0 | 0 |

From the above-mentioned physicochemical properties, particularly the high resolution mass spectra, and from the results of X-ray analysis, it has been clarified that $A_3$, $A_4$, $B_2$, $B_3$, $C_1$ and $C_2$ of B-41 have the following plane structural formula:

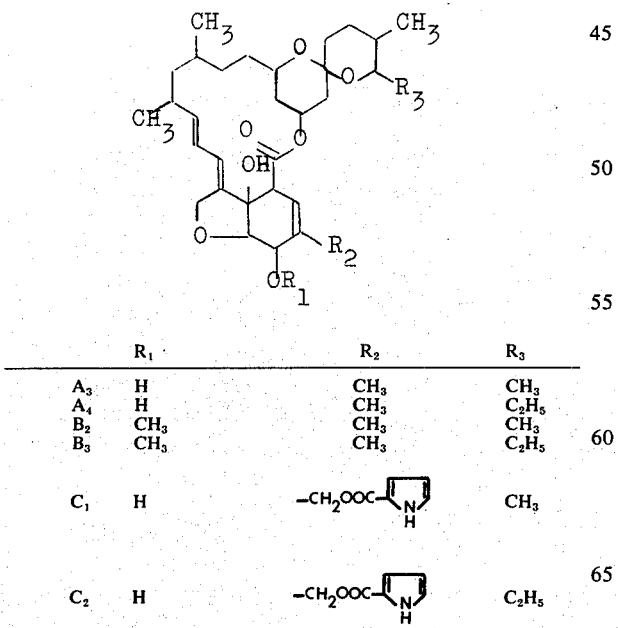

| | $R_1$ | $R_2$ | $R_3$ |
|---|---|---|---|
| $A_3$ | H | $CH_3$ | $CH_3$ |
| $A_4$ | H | $CH_3$ | $C_2H_5$ |
| $B_2$ | $CH_3$ | $CH_3$ | $CH_3$ |
| $B_3$ | $CH_3$ | $CH_3$ | $C_2H_5$ |
| $C_1$ | H | $-CH_2OOC-\langle N-H \rangle$ | $CH_3$ |
| $C_2$ | H | $-CH_2OOC-\langle N-H \rangle$ | $C_2H_5$ |

Likewise, it has been clarified that $A_1$ of B-41 has the following plane structural formula:

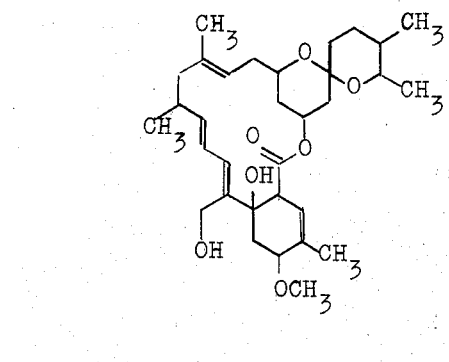

The structures of $A_2$ and $B_1$ of B-41 are not clear. From the fragmentation of mass spectra, however, it is inferred that they are similar in chemical structure to the above-mentioned substances $A_1$, $A_3$, $A_4$, $B_2$, $B_3$, $C_1$ and $C_2$.

Since there are no known antibiotic substances having the aforesaid chemical structures and physicochemical properties, it has been clarified that the B-41 of the present invention is a novel antibiotic substance.

The B-41-146 strain of the genus *Streptomyces*, which produces the antibiotic substance B-41, has such mycological properties as mentioned below.

1. Morphological characteristics:

On most common laboratory media, long, aerial mycelium developed from fine branched substrate mycelium and formed whorls with spirals or loops.

Fragmentations of mycelium not observed at early stage.

Spores more or less short warty, $0.6–0.9 \times 1.1–1.5\ \mu$, formed in chains with 10–50 conidia.

Relatively short warty extrusions on surfaces of spores.

Sporangia and sclerotia not observed.

2. Cultural characteristics on various media:
   i. Sucrose-nitrate agar:
      Good growth; substrate mycelium colorless; reverse pale-brown; aerial mycelium scant, semi-transparent, coriaceous; soluble pigment pale-brown.
   ii. Glucose-asparagine agar:
      Abundant growth; substrate mycelium colorless; reverse pale-brown; aerial mycelium abundant, gray-colored; soluble pigment pale-brown.
   iii. Glycerol-asparagine agar:
      Abundant growth; substrate mycelium colorless; reverse pale-brown; aerial mycelium white, and on slant, many bright grayish brown dots formed in white background; soluble pigment yellowish gray.
   iv. Inorganic salts-starch agar:
      Abundant growth, substrate mycelium colorless; reverse yellowish gray; aerial mycelium gray, and on slant, many pale yellowish dots formed in gray background; soluble pigment bright olive gray.
   v. Tyrosine agar:
      Abundant growth; substrate mycelium grayish yellow brown; reverse brown; aerial mycelium gray, and on slant, yellowish gray dots formed sometimes in gray background; soluble pigment bright brown.
   vi. Nutrient agar:
      Poor growth; substrate mycelium colorless; reverse pale-brown; aerial mycelium scant, white; soluble pigment not produced.
   vii. Yeast extract-malt extract agar:
      Abundant growth; substrate mycelium grayish yellow brown; reverse yellowish brown; aerial mycelium abundant, gray and on slant, many pale yellow dots formed in gray background; soluble pigment yellow.
   viii. Oatmeal agar:
      Abundant growth; substrate mycelium colorless; reverse olive gray; aerial mycelium gray, and on slant, pale yellow dots formed; soluble pigment pale olive.

3. Physiological characteristics:
   i. Growth temperature range: 18°–37°C.
      Optimum growth temperature: 25°–30°C.
   ii. Liquefaction of gelatin: Slow but strongly positive.
   iii. Hydrolysis of starch: Strongly positive.
   iv. Coagulation of skim milk: Positive (28°C).
      Peptonization of skim milk: Positive (28°C)
   v. Melanin formation: Negative.
   vi. Reduction of nitrate: Positive.
   vii. Utilization of various carbon sources (Pridham and Gottlieb agar)
      Utilization degree:
      +++ Raffinose.
      ++ D-Glucose, D-Fructose, Sucrose, L-Rhamnose, I-Inositol, D-Mannitol.
      + L-Arabinose, D-Xylose.

From the above characteristics, this strain is most closely related to *Streptomyces chattanoogensis* (International Journal of Systematic Bacteriology, Vol. 18, No. 2, page 97 (1968)), but differs from B-41-146 strain as follows:

1. The B-41-146 strain abundantly formed whorl, whereas *S.chattanoogensis* monopodially branched.
2. The spore surface of the B-41-146 strain in warty, whereas that of *S.chattanoogensis* is spiny.
3. On yeast-malt extract agar and inorganic salt-starch agar, the B-41-146 strain formed pale-yellow dots in gray background, but *S.chattanoogensis* not formed.
4. The B-41-146 strain assimilates L-arabinose, D-xylose and I-inositol, whereas *S.chattanoogensis* does not assimilate these carbon sources.

In view of the above-mentioned 4 differences in mycological properties, we judged that the B-41-146 strain is a new species of the genus Streptomyces. The B-41-146 strain has been deposited at the Research Institute of Industrial Technology of Microorganisms, Agency of Industrial Science and Technology in Japan, with the deposition number *Bikokenkinki* No. 1438 and at the U.S. Department of Agriculture, Northern Research Laboratory, Peoria, Illinois, with the deposit designation NRRL 5739 on May 25, 1973.

As is well known, actinomycetes tend to cause mutation in the natural world and by application of such artificial operations as, for example, ultraviolet irradiation, radiation irradiation, chemical treatment, etc. The same is the case with the B-41-146 strain of the present invention. The B-41-146 strain referred to in the present invention includes all such mutants. That is, in the present invention, all strains which produce the antibiotic substance B-41 and which are not clearly distinguishable from the B-41-146 strain and mutants thereof are included in the B-41-146 strain.

In the process of the present invention, the antibiotic substance B-41 is obtained by culturing the B-41-146 strain in a proper medium, and then recovering the resulting substance from the medium. The strain may be cultured according to stationary culture but, in case the antibiotic substance is desired to be produced in large quantities, it is most preferable to culture the strain according to liquid culture with aeration and agitation.

As the culture media, there may be used all those which are ordinarily used for the culture of strains belonging to the genus *Streptomyces*. Examples of suitable carbon sources include starch, dextrin, glucose, maltose, corn steep liquor and molasses, and examples of suitable nitrogen sources include meat extract, peptone, yeast extract, soybean meal, casein, ammonium sulfate and ammonium nitrate. If necessary, there may be added potassium, calcium, magnesium, iron, copper, zinc, manganese, cobalt and the like inorganic salts, or minor elements.

For recovery of the antibiotic substance B-41 from the broth, there is adopted such a conventional procedure as extraction with an organic solvent in the presence or absence of an adsorbent or auxiliary agent. In this case, the cells may be separated by filtration from the broth and then extracted with such organic solvent as methanol or acetone, or the broth may directly be subjected to extraction with such organic solvent as chloroform, ethyl acetate, benzene, n-hexane or cyclohexane.

For purification of an oily crude B-41 obtained by removing the solvent from the extract, there is adopted a known purification procedure such as column chromatography or extraction with solvent.

The present invention is illustrated in detail below with reference to examples, but it is needless to say that the scope of the invention is not limited to the examples.

In the examples, the activity of the broth was evaluated according to dipping of two-spotted spider mites. That is, kidneybean leaves parasitized with two-spotted spider mites were dipped for 1 minute in a 70% acetone extract of the broth or in an aqueous dilution thereof and then air-dried, and the acaricidal activity after 24 hours was measured to determine the activity.

EXAMPLE 1

30 Liters of a liquid culture medium (pH of about 7.2) containing 2.0% of glucose, 1.0% of soybean meal and 0.2% of sodium chloride was charged into a 50 liter-jar fermentor, and then sterilized by heating. The B-41-146 strain was inoculated in the said medium and subjected to aerobic stirring culture under such conditions as a temperature of 28°C., an aeration of 8 liters/min. and an agitation of 250 r.p.m. When the cultivation was continued for 120 hours, the broth came to exhibit a brilliant yellow color. At this stage, the cultivation was discontinued, and the activity was examined. As the result, a 300 times dilution of the broth showed an acaricidal activity of 100%. Subsequently, the cells were separated by filtration from the broth and extracted with acetone, and then the acetone was removed by distillation to obtain 44 g. of a brown substance. This substance was extracted with hot hexane, and then the hexane was removed by distillation. The residue was dissolved in a small amount of methanol, and the resulting solution was allowed to stand overnight at −20°C. to deposit precipitates, which were then removed. Thereafter, the methanol was removed by distillation to obtain 35 g. of a brown oily substance. The thus obtained oily substance was subjected to alumina column chromatography and eluted with chloroform, effective fractions were collected according to acaricidal activity, and then the chloroform was concentrated. This operation was repeated several times to obtain 8.2 g. of a crude substance. The acaricidal activity of the crude substance was 100% when used at a concentration of 2 $\mu$g/ml.

The crude substance was passed through a column packed with "Sephadex LH-20" (trade name for a product of Pharmacia Co.) and eluted with methanol, whereby $A_2$, $B_1$, $B_2$, $A_3$ and $A_1$, which are the main component of B-41, were eluted in this order. However, these substances had overlapped with each other and hence were separately recovered in the form of 2 groups of $B_1+A_2$ and $B_2+A_1+A_3$. The $B_1+A_2$ group was subjected to silica gel column chromatography and then eluted with chloroform-ethyl acetate to obtain 210 mg. of $B_1$ and 115 mg. of $A_1$, and the $B_2+A_1+A_3$ group was subjected to silica gel column chromatography to obtain 200 mg. of $B_2$ and 30 mg. of $B_3$, which was similar to $B_2$. Subsequently, the remaining $A_1+A_3$ group was subjected to alumina column chromatography to obtain 372 mg. of $A_1$, 42 mg. of $A_3$ and 15 mg. of $A_4$, which was similar to $A_3$. Further, the alumina column, through which the aforesaid brown oily substance had been passed, was repeatedly subjected several times to methanol elution and silica gel column chromatography to obtain 78 mg. of $C_1$ of B-41 and 52 mg. of $C_2$ of B-41.

For preparation of the insecticidal and acaricidal composition of the present invention, one or more of the thus obtained substances $A_1$, $A_2$, $A_3$, $A_4$, $B_1$, $B_2$, $B_3$, $C_1$ and $C_2$ of B-41 are diluted with a carrier and, if necessary, incorporated with other auxiliary agents, whereby the said substances can be formulated into any of dusts, granules, fine granules, wettable powders, emulsifiable concentrates, oil sprays, etc. It is needless to say that the purification may be discontinued at an optional stage of purification and the resulting, crude substance, which has not completely been purified, may be used as the active ingredient. In case such crude substance is desired to be used as it is as the active ingredient, it is sufficient that the crude substance is purified so as to attain an acaricidal activity of 100% at the concentration of 5 p.p.m. In this case, the content of B-41 in the crude substance is about 50%, and the remainders are impurities from the broth.

The carrier referred to herein means a synthetic or natural inorganic or organic substance which is added to an insecticide in order to make the active ingredient thereof easy to reach the objectives such as plants, mites, harmful insects, etc., or to facilitate the storage, transportation or handling of the active ingredient.

Examples of suitable solid carriers include inorganic substances such as clay, talc, diatomaceous earth, kaolin, bentonite, calcium carbonate and synthetic calcium silicate; natural and synthetic resins such as coumarone resins, alkyd resins and polyvinyl chloride; waxes such as carnauba wax and paraffin wax; shells of nuts such as walnuts and coconuts; and soybean flour.

Examples of suitable liquid carriers include water; alcohols such as ethanol, isopropanol and ethylene glycol; glycol ethers such as ethylene glycol monophenyl ether, and diethylene glycol monoethyl ether; ketones such as acetone, methyl isobutyl ketone, cyclohexanone, acetophenone and isophorone; ethers such as tetrahydrofuran and dioxane; aromatic hydrocarbons such as benzene, toluene, xylene and methyl naphthalene; chlorinated hydrocarbons such as trichloroethylene and carbon tetrachloride; and low, medium and high boiling petroleum fractions containing kerosine, light oils or aromatic hydrocarbons.

Examples of suitable propellants include Furon gases, liquefied petroleum gases, methyl ether and vinyl chloride monomers.

For emulsifying, dispersing, wetting or spreading, there is used a surface active agent, which may be ionic or nonionic. Examples of suitable anionic surface active agents include sodium and calcium salts of lignosulfonic acid, sodium and potassium salts of oleic acid, sodium salt of laurylsulfonic acid, and sodium and calcium salts of dodecylbenzenesulfonic acid. Examples of suitable cationic surface active agents include higher aliphatic amines and ethylene oxide condensates of higher aliphatic amines. Examples of suitable nonionic surface active agents include glycerides of fatty acids, sucrose esters of fatty acids, ethylene oxide condensates of higher aliphatic alcohols, ethylene oxide condensates of higher fatty acids, ethylene oxide condensates of alkyl phenols and alkyl naphthols, and copolymers of ethylene oxide with propylene oxide.

The insecticidal and acaricidal composition of the present invention may contain a protective colloid agent such as gelatin, gum arabic, casein, polyvinyl alcohol or carboxymethyl cellulose, or a thixotropy agent such as sodium polyphosphate or bentonite. The composition of the present invention may further contain other compound having insecticidal and acaricidal activities such as, for example, 2-(1-methylpropyl)-4,6-dinitrophenyl-$\beta,\beta$-dimethyl acrylate, di-(p-chlorophenyl)-cyclopropylcarbinol, N'-(2-methyl-4-chlorophenyl)-N,N-dimethylformamidine, 2,4,4',5-tetrachlorodiphenylsulfone, 1,1-bis(p-chlorophenyl)-2,2,2-trichloroethanol, O,O-diethyl-S-(2-ethylthio)ethyl phosphorodithioate, O,O-dimethyl-S-(N-methyl-N-formylcarbamoylmethyl)phosphorodithioate, 2-sec-butylphenyl-N-methylcarbamate or m-tolyl-N-methylcarbamate, or a mineral oil, whereby the effects of the composition are more increased and, in some cases, synergistic effects may be expected. It is needless to say that the composition of the present invention may be used in admixture with any of fungicides, herbicides, plant growth regulators, attractants, fertilizers, etc.

Effects of the insecticidal and acaricidal compositions of the present invention are explained below with reference to test examples.

TEST EXAMPLE 1

Each of emulsifiable concentrates containing 20% of each of $A_1$, $A_2$, $A_3$, $A_4$, $B_1$, $B_2$, $B_3$, $C_1$ and $C_2$ of B-41, which had been isolated according to the same procedure as in Example 1, was diluted to a given concentration to prepare a chemical solution. Kidneybean leaves infested with two-spotted spider mites were dipped for 1 minute in the above-mentioned chemical solution and then air-dried, and the acaricidal activity (%) after 24 hours was calculated. The results obtained were as set forth in the following table:

| Concentration (p.p.m.) Fraction | 20 | 10 | 5 | 2.5 | 1.25 | 0.63 | 0.31 | 0.16 | 0.08 | 0.04 |
|---|---|---|---|---|---|---|---|---|---|---|
| $A_1$ | 100 | 100 | 100 | 19.9 | 0 | | | | | |
| $A_2$ | 100 | 100 | 100 | 67.6 | 0 | | | | | |
| $A_3$ | 100 | 100 | 100 | 100 | 100 | 100 | 100 | 98.2 | 100 | 15.2 |
| $A_4$ | 100 | 100 | 100 | 100 | 100 | 100 | 100 | 100 | 100 | 21.3 |
| $B_1$ | 98.1 | 81.5 | 69.2 | 20.0 | 0 | | | | | |
| $B_2$ | 100 | 100 | 100 | 100 | 100 | 100 | 80.5 | 16.6 | 0 | |
| $B_3$ | 100 | 100 | 100 | 100 | 100 | 100 | 100 | 74.1 | 18.3 | 0 |
| $C_1$ | 100 | 100 | 100 | 100 | 100 | 100 | 100 | 100 | 100 | 51.8 |
| $C_2$ | 100 | 100 | 100 | 100 | 100 | 100 | 100 | 100 | 100 | 97.3 |
| Reference* | 100 | 56.4 | 0 | | | | | | | |

*1,1-Bis-(p-chlorophenyl)-2,2,2-trichloroethanol (trade name, "Kelthane")

TEST EXAMPLE 2

An emulsifiable concentrate containing 20% of a of a crude B-41, which had been obtained by purifying two times according to alumina column chromatography the brown oily substance prepared in Example 1, was diluted to a given concentration to prepare a chemical solution. This chemical solution was sprayed to apple leaves infested with about 100 European red mites and, 5 days thereafter, the number of living mites was counted. The results obtained were as set forth in the following table:

| | 200 p.p.m. | 100 p.p.m. | 50 p.m.m. |
|---|---|---|---|
| Crude B-41 | 5/108 | 14/121 | 50/115 |
| Reference (Kelthane) | 0/97 | 8/103 | 56/128 |
| Non-treated | | 88/102 | |

(The numerator shows the number of mites before spraying, and the denominator shows the number of living mites at the time of counting.)

TEST EXAMPLE 3

Each of emulsifiable concentrates containing 20% of each of a crude B-41 [which had been obtained by purifying according to silica gel column chromatography the brown oily substance prepared in Example 1] and a crude $A_1+A_2+A_3$ mixture [which had been obtained by subjecting the said crude B-41 to column chromatography using a mixed solvent comprising ethyl acetate and benzene (50:50)] was diluted to a given concentration to prepare a chemical solution. This chemical solution was sprayed to orange leaves infested with citrus red mites, and the acaricidal activity (%) after 24 hours was calculated. The results obtained were as set forth in the following table:

| | 20 p.p.m. | 10 p.p.m. | 7 p.p.m. | 3.3 p.p.m. |
|---|---|---|---|---|
| Crude B-41 | | 100% | | 85.5% |
| Crude $A_1+A_2+A_3$ mixture | | 100 | | 100 |
| Reference (Kelthane) | 90.9 | | 30.8 | |

TEST EXAMPLE 4

Each of emulsifiable concentrates containing 20% of each of a crude $A_1+B_1$ mixture B-41 [which had been obtained by purifying 3 times according to silica gel chromatography (n-hexane:acetone = 70:30) the brown oily substance prepared in Example 1] and a crude $A_2+A_3+B_2$ mixture of B-41 [which had been obtained in the same manner as the former] was diluted to a given concentration to prepare a chemical solution. This chemical solution was sprayed to Chinese cabbages infested with green peach aphids, and the mortality (%) of the aphids after 24 hours was calculated. The results obtained were as set forth in the following table:

| | 250 p.p.m. | 25 p.p.m. | 2.5 p.p.m. |
|---|---|---|---|
| Crude $A_1+B_1$ mixture | 100% | 92.3% | 64.2% |
| Crude $A_2+A_3+B_2$ mixture | 100 | 89.8 | 52.8 |

| | 250 p.p.m. | 25 p.p.m. | 2.5 p.p.m. |
|---|---|---|---|
| Reference ** | 100 | 73.1 | 33.1 |

** O,O-Dimethyl-O-(2,2-dichlorovinyl)phosphate

TEST EXAMPLE 5

Eggs of rice stem borer of 1st generation were inoculated to rice plants (variety "Kinmaze"), which had been planted in 200 cm² pots, and were hatched to allow the larvae invade the stems. Subsequently, a wettable powder containing 40% of a crude B-41, which had been obtained by purifying two times according to alumina column chromatography the brown oily substance prepared in Example 1, was diluted to a given concentration and then sprayed to the plants in a proportion of 100 cc. per pot. 5 Days thereafter, the stems were split to examine the alive and dead of the larvae, and the mortality (%) of the larvae was calculated. The results obtained were as set forth in the following table:

| | 100 p.p.m. | 50 p.p.m. |
|---|---|---|
| Crude B-41 | 100% | 79.4% |
| Reference *** | 82.1 | 25.5 |

*** O,O-Diethyl-O-(2-isopropyl-4-methyl-6-pyrimidinyl)phosphorothioate

As seen in Test Examples 1 to 5, the antibiotic substance B-41 is excellent in insecticidal and acaricidal activity, and has far more prominent effects particularly on mites than the conventional chemicals.

Procedures for preparing the insecticidal and acaricidal compositions of the present invention are shown below with reference to preparation examples, in which all parts are by weight.

PREPARATION EXAMPLE 1

10 Parts of a crude B-41, which had been obtained by purifying 2 times according to silica gel column chromatography the brown oily substance prepared in Example 1, was homogeneously mixed with 5 parts of white carbon, 50 parts of talc and 35 parts of clay. The resulting mixture was pulverized three times by means of an impact type pulverizer and again homogenized to obtain a dust.

PREPARATION EXAMPLE 2

40 Parts of the same crude B-41 as in Preparation Example 1 was homogeneously mixed with 20 parts of white carbon, 5 parts of sodium dodecylbenzenesulfonate, 2 parts of polyvinyl alcohol and 33 parts of clay. The resulting mixture was pulverized three times by means of an impact type pulverizer and again homogenized to obtain a wettable powder.

PREPARATION EXAMPLE 3

20 Parts of the same crude B-41 as in Preparation Example 1 was homogeneously mixed with 7 parts of polyoxyethylene nonylphenyl ether, 3 parts of calcium dodecylbenzenesulfonate and 70 parts of xylene, and the resulting mixture was filtered to obtain an emulsifiable concentrate.

PREPARATION EXAMPLE 4

10 Parts of the same crude B-41 as in Preparation Example 1 was dissolved in 10 parts of xylene. The resulting solution was mixed with 80 parts of machine oil and then filtered to obtain an oil spray.

What we claim is:

1. A compound having the formula

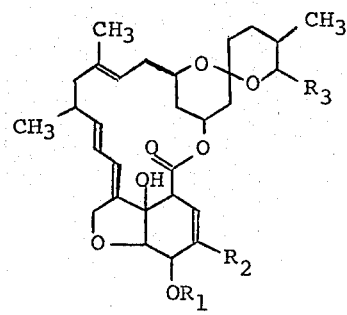

wherein $R_1$ represents a hydrogen atom or methyl, $R_2$ represents methyl and $R_3$ represents methyl or ethyl.

2. The compound according to claim 1 wherein $R_1$ is hydrogen atom, $R_2$ is methyl group and $R_3$ is methyl group.

3. The compound according to claim 1 wherein $R_1$ is hydrogen atom, $R_2$ is methyl group and $R_3$ is ethyl group.

4. The compound according to claim 1 wherein $R_1$ is methyl group, $R_2$ is methyl group and $R_3$ is methyl group.

5. The compound according to claim 1 wherein $R_1$ is methyl group, $R_2$ is methyl group and $R_3$ is ethyl group.

6. A compound having the formula

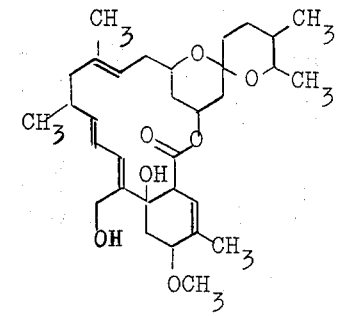

* * * * *

UNITED STATES PATENT OFFICE
CERTIFICATE OF CORRECTION

PATENT NO. : 3,950,360
DATED : April 13, 1976
INVENTOR(S) : ATSUSHI AOKI et al

It is certified that error appears in the above-identified patent and that said Letters Patent are hereby corrected as shown below:

Column 5, line 45:

delete the formula of the compound and replace with

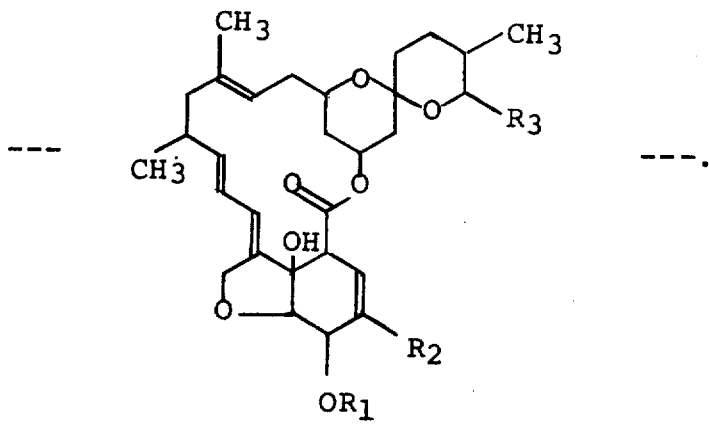

Column 10, line 48:

replace "Furon" with --- Freon ---.

Column 12, line 8:

replace "numerator" with --- denominator ---.

Column 12, line 9:

replace "denominator" with --- numerator ---.

Column 13, line 13:

before "invade", insert --- to ---.

UNITED STATES PATENT OFFICE
CERTIFICATE OF CORRECTION

PATENT NO. : 3,950,360
DATED : April 13, 1976
INVENTOR(S) : ATSUSHI AOKI et al

It is certified that error appears in the above-identified patent and that said Letters Patent are hereby corrected as shown below:

Columns 1 and 2, last line:

delete "$B_1$ $B_2$ $B_3$ $C_1$ $C_2$".

Columns 3 and 4, first two lines:

delete first two lines in entirety, and replace with --- $B_1$ $B_2$ $B_3$ $C_1$ $C_2$ ---.

Column 4, line 66:

replace "omitted" with --- emitted ---.

Signed and Sealed this

Twenty-third Day of November 1976

[SEAL]

Attest:

RUTH C. MASON
*Attesting Officer*

C. MARSHALL DANN
*Commissioner of Patents and Trademarks*